United States Patent [19]
Daleke

[11] Patent Number: 5,972,380
[45] Date of Patent: Oct. 26, 1999

[54] AMINOPHOSPHOLIPID COMPOSITIONS AND USES THEREOF

[75] Inventor: David L. Daleke, Bloomington, Ind.

[73] Assignee: Indiana University Foundation, Bloomington, Ind.

[21] Appl. No.: 09/098,102

[22] Filed: Jun. 16, 1998

Related U.S. Application Data

[62] Division of application No. 08/735,193, Oct. 21, 1996, Pat. No. 5,767,298, which is a continuation of application No. 08/195,216, Feb. 14, 1994, abandoned.

[51] Int. Cl.$^6$ .................................................... A61K 9/127
[52] U.S. Cl. ........................... 424/450; 424/1.21; 554/79; 554/80; 935/54

[58] Field of Search ........................ 424/450, 1.2, 9.32, 424/9.51; 554/79, 80; 935/54

[56] References Cited

U.S. PATENT DOCUMENTS

4,983,397  1/1991  Schroit ..................................... 424/450

Primary Examiner—Gollamudi S. Kishore
Attorney, Agent, or Firm—Woodard, Emhardt, Naughton Moriarty & McNett

[57] ABSTRACT

Described are reversibly N-acylated phosphotidylserine and phosphatidylethanolamine derivatives which are useful as caged aminophospholipids. Also described are pharmaceutical preparations containing pH-sensitive liposomes formed with the caged aminophospholipids, and related methods.

15 Claims, 4 Drawing Sheets

AMINOPHOSPHOLIPID COMPOSITIONS AND USES THEREOF

The present application is a divisional of U.S. patent application Ser. No. 08/735,193, filed Oct. 21, 1996, now U.S. Pat. No. 5,767,298, which is a continuation of U.S. patent application Ser. No. 08/195,216, filed Feb. 14, 1994, now abandoned.

BACKGROUND

The present invention relates generally to compositions and methods involving aminophospholipids, and more particularly to pH-dependent caged aminophospholipids, liposomes formed with the caged aminophospholipids, and pharmaceutical preparations containing such liposomes.

As further background, all biological membranes display an asymmetric transmembrane orientation of the four major classes of phospholipids. Generally, the amine-containing phospholipids, phosphatidylserine (PS) and phosphatidylethanolamine (PE) are enriched in the cytofacial monolayer, while the choline-containing phospholipids, phosphatidylcholine (PC) and spingomyelin (SM) are found on the opposite face of the membrane (Bretscher, 1973; Verkleij et al., 1973; Rothman & Lenard, 1977). This asymmetry is maintained by slow passive transmembrane flip-flop (Kornberg & McConnell, 1971; Van Meer & Op den Kamp, 1982; Homan & Pownall, 1988; Middlekoop et al., 1986), binding of acidic lipids to inner monolayer proteins (Haest et al., 1978; Franck et al., 1985) and by the selective, ATP-dependent, inward transport of aminophospholipids (Devaux, 1991; Schroit & Zwaal, 1991).

The aminophospholipid transporter, or "flippase," requires Mg2+-ATP and is inhibited by vanadate, calcium, and sulfhydryl reagents (Seigneuret & Devaux, 1984; Daleke & Huestis, 1985; Connor & Schroit, 1987; Bitbol et al., 1987). The enzyme displays an absolute specificity for lipid headgroup structure. The flippase transports amine-containing phospholipids exclusively and has an affinity for PS approximately ten-fold greater than for PE (Zachowski et al., 1986). Alkylating the amine function, esterifying the carboxyl group, or increasing the distance between the phosphate and carboxyl/amine groups results in reduced flippase activity (Morrot et al., 1989; E. Nemergut, M. Zimmerman and D. Daleke, unpublished observations). Transport is dependent on the configuration of the glycerol backbone. Removing the sn-2 fatty acyl group (Daleke & Huestis, 1985), inverting the stereochemistry in the sn-2 position (Martini & Pagano, 1987), or replacing the diacylglycerol moiety with ceramide (Morrot et al., 1989) reduces considerably the transport of aminophospholipids. In contrast, transport activity is relatively insensitive to acyl chain length (Daleke & Huestis, 1985), although hydrophilic fluorescent fatty acyl substituents result in reduced transport rates (Colleau et al., 1991). The relative insensitivity of the flippase to acyl chain length and composition has allowed the design of PS substrates labeled with a variety of acyl chain reporter groups. In addition to short (Daleke & Huestis, 1985) and long (Tilley et al., 1986) chain radiolabeled fatty acids, spin label (Seigneuret & Devaux, 1984) and fluorescent (Connor & Schroit, 1987) fatty acids have been used to measure flippase activity. The strategy behind the design of these labeled lipids is that they are relatively hydrophilic and will rapidly and spontaneously exchange from donor vesicles to cell membranes. The transmembrane distribution is subsequently assessed by extracting outer monolayer lipid into albumin or exogenous acceptor vesicles. The amount of spin, fluorescent, or radiolabeled lipid remaining in the cell is considered the amount of lipid transported to the inner monolayer.

The measurement of transport kinetics required that the rate of lipid incorporation be faster than the rate of transport. These measurements have been confounded by concurrent incorporation and transport of lipid probes. One solution is prior inhibition of the flippase by using a reversible inhibitor such as vanadate, a sulfhydryl reagent, or low temperatures. This obviates the need for rapid lipid incorporation, however these methods are complicated by relatively slow reversal of inhibition (sulfhydryl reagents) or slow lipid incorporation (low temperatures).

In another facet, the use of liposomes as drug delivery systems has been explored for some time. A primary problem in liposomal delivery has been the inability to effectively release liposomal contents into the cell cytoplasm: most liposomes are taken up by cells into endosomes, low pH membrane compartments within the cell. To overcome these problems, the applicant has designed and synthesized reversibly N-modified or "caged" aminophospholipids. These lipids are N-acylated with structural analogs of maleic anhydride, which can be released by exposure to low pH solutions. The lipids can be incorporated into the liposomes to create pH-sensitive liposomes which can be used to effectively deliver active agents such as pharmaceuticals to cellular cytoplasm; and can also be used in labeling cells and the study of enzymatic activity such as flippase activity.

SUMMARY OF THE INVENTION

One object of the invention is to provide caged aminophospholipid compounds which are pH sensitive in physiologically relevant pH ranges.

Another object of the invention is to provide pH-sensitive caged aminophospholipids which can be prepared utilizing readily available reagents.

Another object of the invention is to provide liposomes incorporating active agent wherein the liposomes are pH-sensitive due to the incorporation of pH-sensitive caged aminophospholipids of the invention.

Another invention of the invention is to provide facile methods for preparing pH-sensitive, active agent-containing liposomes.

Another object of the invention is to provide pharmaceutical preparations which include active agent-containing, pH-sensitive liposomes suspended in an acceptable carrier.

These and other objects are provided in preferred embodiments of the invention, one of which provides an aminophospholipid compound of the formula I or II:

I

-continued

II wherein
Z=—CH$_2$— or —C(H)(COO$^-$)—;
Y=—H or lower alkyl; and
R$^1$ and R$^2$, which may be the same or may differ from one another, are each a fatty acid group;
or a fluorescent-, radioactive- or spin-labelled derivative thereof.

Another preferred embodiment of the invention provides a pH-sensitive liposomal delivery system, comprising a liposome containing an active agent, said liposome being formed with one or more aminophospholipids having the formula I or II above.

Another preferred embodiment of the invention provides a pharmaceutical preparation comprising a suspension of liposomes containing an active agent in a pharmaceutically acceptable carrier, said liposomes being formed with one or more aminophospholipids having the formula I or II above.

Still another preferred embodiment of the invention provides a method of introducing a modified aminophospholipid into a cell, comprising contacting the cell with an aminophospholipid compound of the formula I or II above.

Additional objects, features and advantages of the invention will be apparent from the following description.

BRIEF DESCRIPTION OF THE DRAWINGS

FIGS. 3A and B show the kinetic parameters for the pH-dependent cleavage of C-DOPE and C-DOPS. C-DOPE (0.5 mM, column 1) and C-DOPS (0.5 mM, columns 2–5) were suspended in citrate buffer, pH 5.5 (columns 1 and 2) containing Triton X-100 (0.1%, column 3), NaCl (1 M, column 4) or egg PC (2.5 mM, column 5) and incubated for 1 h at 37° C. The extent of cleavage was quantitated by phosphate determination of thin layer chromatographic separations of extracted lipids. Kinetic parameters were determined by non-linear least squares fits of the data to a double exponential equation (see FIG. 2): A. Exponential coefficient α1 (open bars) and α2 (filled bars) B. Time constants τ1 (open bars) and τ2 (filled bars).

FIGS. 4A and B show the incorporation, uncaging, and transport of C-DOPS in human erythrocytes. A. Timecourse of erythrocyte shape change (morphological index) induced in washed human erythrocytes by C-DOPS liposomes (200 μM) incubated at HBS. At 45 min (arrow), one set of cells was centrifuged, resuspended in citrate buffer (100 mM, pH 5.5) and re-incubated at 37° C. (open circles). Aliquots were fixed with glutaraldehyde and analyzed by light microscopy. B. Low pH-induced cleavage of C-DOP$^3$HS in human erythrocytes. Washed human red cells were treated with C-DOP$^3$HS (55 nCi) for 45 min at 37° C. in HBS. After centrifugation , the cells were resuspended in citrate buffer (pH 5.5) and reincubated at 37° C. At the indicated timepoints, lipids were extracted from aliquots of cells, C-DOP$^3$HS and DOP$^3$HS were separated by thin layer chromatography, and radiolabeled lipids were quantitated by scintillation counting.

DESCRIPTION OF THE PREFERRED EMBODIMENT

For the purpose of promoting an understanding of the principles of the invention, reference will now be made to certain embodiments thereof and specific language will be used to describe the same. It will nevertheless be understood that no limitation of the scope of the invention is thereby intended, each alterations, further modifications and applications of the principles of the invention as illustrated herein being contemplated as would normally occur to one skilled in the art to which the invention relates.

As indicated above, the present invention provides pH-sensitive, caged aminophospholipids of the formula I or II:

I

-continued wherein
Z=—CH$_2$— or —C(H)(COO$^-$)—;
Y=—H or lower alkyl; and
R$^1$ and R$^2$, which may be the same or may differ from one another, are each a fatty acid group;
or a fluorescent-, radioactive- or spin-labelled derivative thereof.

The invention thus provides phosphatidylethanolamine (i.e. where Z is —CH$_2$) and phosphatidylserine (where Z is —C(H)(COO$^-$)—) derivatives. To prepare such derivatives, the native phosphatide can be acylated with the appropriate anydride (maleic acid derivative or phthalic acid). Such reactions are desirably performed under dry conditions in an appropriate inert organic solvent such as presence of a base, under an inert atmosphere such as nitrogen. The acylation reactions can be of a duration of, for example, several hours or several days, and can be monitored for completion using conventional techniques such as thin-layer chromatography.

Preferred caged aminophosphospholipids of the invention occur within formula I above wherein Y is lower alkyl (i.e. C$_1$ to C$_5$ alkyl), e.g. methyl, ethyl, n-propyl, iso-propyl, n-butyl, iso-butyl, tert-butyl, or pentyl. Such caged aminophospholipids, e.g. the citroconyl derivatives described in the Experimental, exhibit desirable properties related to pH-sentivity. In particular, such derivatives have been found to be particularly sensitive within the most desirable physiological pH range of about 5.5 to about 8, becoming substantially uncaged (i.e. the N-acyl group is cleaved) within this range.

Caged aminophospholipids of the invention are successfully incorporated into mammalian cells, e.g. erythrocytes. At relatively higher pH's, the caging groups prevent recognition of the caged aminophospholipids by flippase and thus the aminophospholipids remain in the outer monolayer. Subjection of the cells to lower pH's cleaves the caging groups to release the native aminophospholipids which are then recognized and transported by flippase. Caged aminophospholipids of the invention can thus incorporate labels in the fatty acyl chains or in the headgroup, e.g. a spin, radioactive or fluorescent label (see e.g., Daleke & Huestis, 1985; Tilley et al., 1986; Seigneuret & Devaux, 1984; and Connor & Schroit, 1987), and be used to label cells in various diagnostic and other procedures.

Caged aminophospholipids of the invention exhibit increased water solubility as compared to corresponding native phospholipids, leading to increased intermembrane exchange of the aminophospholipids. Caged aminophospholipids having relatively long fatty acid chains can thus be more successfully incorporated and exchanged, affording a greater range of effectively utilizable aminophospholipids than previously available.

As well, the caged properties of the inventive aminophospholipids will enable the study of transport proteins such as flippase, and can serve to rapidly provide a lipid activator or substrate to enzymes such as protein kinase C (Newton & Koshland, 1989, 1990), factor VIII of the blood clotting cascade (Gilbert et al., 1992), the prothrombinase complex (Gerads et al., 1990; Krishnaswamy, 1990), the Na+/K+ pump (Wheeler & Whitman, 1970; Harris, 1985), and the plasma membrane Ca2+-ATPase (Niggli et al., 1981 a,b), all of which are activated by phosphatidyl serine (PS). The reversible modification of PS will allow the rapid controlled activation of these enzymes or transporters by PS.

The present invention also provides for the administration of active agent-containing liposomes to mammals. In this regard, it will be understood that the active agent employed may be selected from any of the many known active agents which can be incorporated into liposomes, for example including pharmaceutical agents, antimitotic agents, antibiotic agents, antifungal agents, ribozymes, antisense oligonucleotides, genes for gene therapy, and the like. Preferred active agents will be water soluble materials, which can be conveniently incorporated into the liposomes, although water-insoluble agents can also be suitably incorporated by known methods.

Generally, the preparation of liposomes for drug delivery is known, and the liposomes of the present invention can be prepared utilizing conventional techniques. For example, multilamellar vesicles can be prepared by adding lipid materials to aqueous solutions, followed by vortexing. Unilamellar vesicles can then be made by sonication of the resulting multilamellar vesicles, if desired. Dried lipid materials may also be dissolved in ethanol and injected into warm aqueous solution to form "ethanol-injected" liposomes. Reverse evaporation vesicles ("REV's) are also well known, and can be prepared by dissolving dried lipid materials in ether, adding an aqueous solution of the drug or active agent to be incorporated to the ether solution, and vortexing the resulting two-phase material to form a stable emulsion. The emulsion is then rotary evaporated to evaporate the ether so as to form the REV's. If desired, the resulting REV's can be extruded through membranes having selected pore sizes to provide advantageous size distributions.

Liposomes of the invention will contain aminophospholipids of the invention in an effective amount to render the liposomes pH-sensitive, so that once endocytosed into target cells the caging groups are cleaved thus resulting in destabilization of the liposome (when the uncaged aminophospholipids become fusogenic) and release of the active agent into the cell cytosome. Liposomes formed with caged aminophospholipids of the invention can also contain other lipid components such as phosphatidyl cholines, phosphatidylserines, phosphotidylethanolamines, and cholesterol, which are conventionally used in liposome formation.

It will be understood that the liposomes can be administered in suitable pharmaceutical preparations. Such pharmaceutical preparations may include, for example, pharmaceutically acceptable carriers such as sterile aqueous solution and various organic solvents. Pharmaceutical compositions formed by combining liposomes incorporating pH-sensitive aminophospholipids of the invention and the pharmaceutically acceptable carriers are then easily administered in a variety of dosage forms such as injectable solutions.

For parenteral administration, suspensions of liposomes in sterile aqueous medium (desirably isotonic) may be employed. These aqueous suspensions are especially suitable for intravenous administration. In this connection, sterile aqueous media which can be employed will be known to those of skill in the art in light of the present disclosure. In all cases for parenteral administration the preparation to be administered must be sterile and must be fluid to the extent that easy syringability exists. It must be stable under the conditions of manufacture and storage and must be preserved against the contaminating action of microorganisms, such as bacteria and fungi. The proper fluidity can be maintained, for example, by the maintenance of the required particle size and by altering lipid composition.

The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars or sodium chloride.

Sterile injectable solutions can be prepared by suspending the active agent-containing liposomes in the required amount in the appropriate liquid medium with various of the other ingredients enumerated above, as required, followed by sterilization, e.g. by radiation or sterile filtration.

As used herein, "pharmaceutically acceptable carrier" includes any and all solvents, dispersion media, antibacterial and antifungal agents, isotonic agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

In order to promote a further understanding of the present invention and its features and advantages, the following specific Experimental is provided. It will be understood that this experimental is illustrative and not limiting of the invention.

EXPERIMENTAL

Abbreviations

The following abbreviations are used herein: ATP—adenosine triphosphate; C-DOPE—N-citraconyl-dioleoylphosphatidylethanolamine; C-DOPS—N-citraconyl-dioleoylphosphatidylserine; C-DLPS—N-citraconyl-dilauroylphosphatidylserine; CM-52—carboxymethyl cellulose cation exchange resin; D-DOPE—N-dimethylmaleyl-dioleoylphosphatidylethanolamine; DLPC—dilauroylphosphatidylcholine; DLPS—dilauroylphosphatidylserine; DOPC—dioleoylphosphatidylchloine; DOPE—dioleoylphosphatidylethanolamine; DOPS—dioleoylphosphatidylserine; DTT—dithiothreitol; FAB—fast atom bombardment (mass spectrometry); HBS—Hepes buffered saline; HCT—hematocrit; Hepes—N-2-hydroxyethylpiperazine-N'-2-ethanesulfonic acid; M-DOPE—N-maleyl-dioleoylphsophatidylethanolamine; MLV—multilamellar vesicle; MI—morphological index; NEM—N-ethylmaleimide; PC—phosphatidylcholine; P-DOPE—N-phthalyl-dioleoylphosphatidylethanolamine; PE—phosphatidylethanolamine; PS—phosphatidylserine; SM—sphingomyelin; T-DOPE—N-3,4,5,6-tetrahydrophthalyl-phosphatidylethanolamine; TLC—thin layer chromatography.

Materials. Dioleoylphosphatidylethanolamine (DOPE), dioleoylphosphatidylserine (DOPS), dioleoylphosphatidylcholine (DOPC), dilauroylphosphatidylserine (DLPS), and dilauroylphosphatidylcholine (DLPC) were obtained from Avanti Polar Lipids (Alabaster, Ala.). Citraconic anhydride, maleic anhydride, dimethylmaleic anhydride, 3,4,5,6-tetrahydrophthalic anhydride, phthalic anhydride, fluorescamine, phospholipase D (cabbage), and 2,6-lutidine were purchased from Sigma (St. Louis, Mo.). Carboxymethyl cellulose cation exchange resin was obtained from Whatman (Hillsboro, Ore.). L-[3-$^3$H] serine was purchased from Amersham (Arlington Height, Ill.). Silica gel HL and HLF TLC plates were purchased from Analtech (Newark, Del.). Unless otherwise noted, all chemicals were reagent grade.

Synthesis and purification of "caged" DOPE derivatives. N-modified DOPE derivatives were synthesized by acylation of DOPE with citraconic, maleic, 3,4,5,6-tetrahydrophthalic, dimethylmaleic, or phthalic anhydride (Scheme 1). All reactants were dried under vacuum for a minimum of 12 h before use. DOPE (25 µmol) was combined with 2,6-lutidine (50 µmol) and the appropriate anhydride (2.5 mmol) in a 3.0 mL vial. The mixtures were stirred under nitrogen until the reactions were complete as indicated by thin-layer chromatography (TLC) and phosphate analysis (Bartlett, 1959). Separated compounds were identified by iodine staining and by reaction of amine containing lipids with fluorescamine spray (0.05% w/v in acetone). The phthalic and maleic reactions were complete in 3 h, the 3,4,5,6-tetrahydrophthalic reaction in 24 h, the dimethylmaleic reaction in 36 h, and the citraconyl reaction in 48 h at room temperature. Initial yields were determined by phosphate analysis of TLC-separated products.

Scheme 1. Formation and cleavage of "caged" aminophospholipids. Phosphatidylserine (I) or phosphatidylethanolamine (not shown) is acylated with structural analogs of maleic anhydride (II: maleic anhydride (IV), citraconic anhydride (V), dimethylmaleic anhydride (VI), tetrahydrophthalic anhydride (VII), and phthalic anhydride (VIII)) to form a pH-labile "caged" aminophospholipid (III).

The derivatives were purified using a combination of ion-exchange and high performance liquid chromatography. The citraconyl-DOPE (C-DOPE) reaction mixture was separated on a carboxymethyl-cellulose (CM-52) cation exchange column (6×250 mm) using a gradient elution of increasing concentration of methanol (0–50%) in chloroform. HPLC was used to purify the cyclic imide of the dimethylmaleyl-DOPE (D-DOPE) and tetrahydrophthalyl-DOPE (T-DOPE) derivatives using an isocratic solvent system (CHCl3:CH3OH:H2O 25:10:1).

Synthesis and purification of citraconyl-DOPS. DOPS (25 μmol) was combined with 2.6-lutidine (50 μmol) and citraconic anhydride (2.5 mmol) in a 3.0 mL vial. All other reaction and purification procedures were the same as those described previously for the C-DOPE derivative. The reaction mixture was loaded onto a CM-52 column (6×250 mm) and eluted with chloroform (150 mL), followed by 50% methanol in chloroform (75 mL). The latter fraction was dried by rotary evaporation, resuspended in chloroform (2 mL), loaded onto a freshly poured CM-52 column, and eluted sequentially with chloroform (150 mL), 30% methanol in chloroform (75 mL), and 50% methanol in chloroform (75 mL). A mixture of citraconyl-DOPS (C-DOPS) and DOPS was collected in the 30% methanol fraction and the pure C-DOPS derivative was collected in the 50% methanol fraction. This final purification step was repeated several times to collect all of the desired product. Citraconyl-DLPS (C-DLPS) was synthesized similarly.

Physical characterization of the purified "caged" compounds. Proton NMR data was collected on a 300 MHz Varian or a 500 MHz Bruker NMR spectrometer. All lipid samples were dissolved in CDCl3:CD3OD (4:1) and referenced to the residual chloroform peak. Mass spectra were collected using negative ion fast atom bombardment mass spectrometry.

Synthesis and purification of citraconyl-dioleoylphosphatidyl-[3-$^3$H]serine. Dioleoylphosphatidyl-L-[3-$^3$H]-serine (DOP$^3$HS) was synthesized from DOPC and L-[3-$^3$H]-serine (40 Ci mol-1) by phospholipase D-catalyzed transphosphatidylation (Juneja et al., 1989). Briefly, 29 μL of a saturated (46% w/v) solution of serine in acetic acid (200 mM) and CaCl2 (40 mM), pH 5.4, was mixed with 46 μL of DOPC (35.6 mM) in diethyl ether and vortexed continuously at 30° C. Phospholipase D (5 IU) was added to the emulsion while vortexing. After 30 min, an additional 5 IU aliquot of enzyme was added to the reaction. Following a 60 min incubation, the ether phase was extracted (Comfurius & Zwaal, 1977) and dried under nitrogen. An additional ether phase, containing DOPC (35.6 mM), was added back to the aqueous phase and the reaction was repeated as described above. After 60 min, the reaction was stopped by the addition of EDTA (39 mM). The lipid products were extracted, the aqueous layer was washed once with two volumes of chloroform, and the combined organic phases were dried under nitrogen. The yield of the reaction was determined by scintillation counting of TLC-separated products.

Citraconyl-DOP³HS was synthesized from citraconic anhydride (22.2 μmol) and DOP³HS (20.4 μCi) in the presence of 2,6-lutidine and purified by CM-52 chromatography as described above.

pH-Dependent cleavage measurements. A chloroform solution of the "caged" aminophospholipid (0.1 μmol) being tested was dried under nitrogen and the lipid was resuspended in buffers (200 μL) of varying pH; pH 3 (50 mM citrate), pH 4.5 (50 mM citrate), pH 6 (50 mM citrate), pH 7 (50 mM Hepes), and pH 8 (50 mM Hepes), adjusted to physiological ionic strength (290–310 mOsM) with NaCl. Solutions were vortexed briefly to make multilamellar vesicles (MLVs) and placed in a shaking water bath for 1 h at 37° C. The reaction was quenched after 1 h with a Hepes buffer (0.5 M, pH 8.0). The lipid was extracted and the aqueous phase washed twice with chloroform. The derivative was separated from DOPE or DOPS by normal phase silica TLC eluted with CHCl3:CH3OH:NH4OH:H2O (65:25:2.5:2.5). The fraction cleaved was determined by phosphate analysis of the corresponding iodine stained spots. A background measurement, not incubated at 37° C. for 1 h, but subjected to the same extraction and TLC procedures, was performed to correct for hydrolysis that occurred during workup. All measurements were completed in triplicate.

Determination of the time course for cleavage. Chloroform solutions of C-DOPS or C-DOPE (0.1 μmol) were dried under nitrogen and resuspended in 200 μL of citrate buffer (50 mM, pH 5.5). MLVs were prepared as described above and placed in a shaking water bath at 37° C. At prescribed time points, the reaction was quenched with 50 μL of Hepes buffer (1 M, pH 8.5), the lipid was extracted, and the amount of cleavage was determined by phosphate analysis of TLC-separated lipids.

In one set of experiments, the ionic strength of the citrate incubation buffer (pH 5.5) was raised by including 1 M NaCl and cleavage was measured as described above. In a second set of experiments, C-DOPS cleavage was measured in the presence of Triton X-100 (0.1%). In a third set of experiments, a five fold excess of DOPC was add to the lipid suspensions to dilute the surface charge. In a fourth set of experiments, ethanol (0.05–0.5%), DTT (5 mM), aniline (1.5 mM), p-nitroaniline (1.5 mM), and DOPE (2.5 mM) were added in separate experiments to the incubation buffers as scavengers of the anhydride. The lipid products were extracted and isolated by thin-layer chromatography as described previously. A single time point at 2.5 or 3 h was analyzed. All measurements were completed in triplicate and data were fit to a biexponential equation $$f(x) = \alpha_1 * \exp(-x/\tau_1) + \alpha_2 * \exp(-x/\tau_2))$$

using the program MacCurveFit (Kevin Raner, Mt. Waverley, Australia).

Isolation of the slowly hydrolyzed component of the C-DOPS and C-DOPE reactions. A chloroform solution of C-DOPE or C-DOPS (10 mg) was dried under nitrogen and resuspended in 1 mL of a citrate buffer (100 mM, pH 5.5). The mixture was sonicated briefly and incubated at 37° C. for 30 min in a shaking water bath. The lipid products were extracted as described previously and purified by CM-52 cation exchange chromatography.

Cells. Human erythrocytes were obtained from healthy adult volunteers by venipuncture and collected into EDTA (3.3 mM final concentration). Erythrocytes were pelleted by centrifugation (5 min, 3000 g), washed three times in Hepes buffered saline (HBS, 118 mM NaCl, 50 mM Hepes, 5 mM KCl, 1 mM MgSO4, 5 mM glucose, pH 8.25), and stored on ice at 50% hematocrit (HCT).

Phosphatidylserine transport assay. Previously washed erythrocytes were pelleted by centrifugation (5 min, 3000 g) and incubated at 50% HCT with sonicated DLPS, DLPC, C-DLPS, or C-DOPS vesicles (200 μM) in HBS according to the method of Daleke and Huestis (1985). At prescribed time points, the cells were fixed by adding 5 μL aliquots to 50 μL of glutaraldehyde (0.5%). Aliquots of fixed cells were examined by light microscopy for changes in cell morphology. Echinocytes were assigned scores of +1 to +5 based on the degree of crenation, discocytes were scored 0, and stomatocytes were given scores of −1 to −4 based on their degree of invagination (Daleke & Huestis, 1989). Echinocytic shapes are indicative of cells with excess lipid in the outer monolayer, while stomatocytic shapes are indicative of cells with excess inner monolayer lipid (Sheetz & Singer, 1974). Thus, cell morphology can be used to measure the movement of exogenously added lipids from the outer to the inner monolayer. The average score of a field of 100 cells is defined as the morphological index (MI).

Hydrolysis of C-DOPS in human erythrocytes. Washed red blood cells were incubated with sonicated C-DOPS vesicles (200 μM) in HBS at 50% HCT for 45 min at 37° C. After 45 min (C-DOPS), the cells were centrifuged (16,000 g, 5 min) and the supernatant was removed. The cells were washed once with a citrate buffer (50 mM, 300 mOsM, pH 5.25) and then incubated at 20% HCT for varying lengths of time in citrate buffer. This treatment resulted in a stable change in pH within 10 min. The final pH of the red cell suspensions in HBS was 7.58±0.02 and those suspensions in citrate buffer was 5.72±0.03 pH units. The values were corrected for temperature (37° C.). At the specified time points, an aliquot of cells was fixed and examined by light microscopy.

Back extraction of dilauroyl phospholipids from human erythrocytes. Washed red blood cells were incubated with DLPS, DLPC, or C-DLPS (200 μM) in HBS at 50% HCT for 90 min at 37° C. After 15 min, an aliquot of the cells was removed and the short chain phospholipids in the outer monolayer were back extracted with sonicated DOPC vesicles (20 mM) in HBS at 5% HCT for 15 min at 37° C. A separate aliquot of C-DLPS-treated cells was removed at 15 min, centrifuged, resuspended in citrate buffer (pH 5.5), and reincubated at 37° C. After 60 min, an aliquot from the cells incubated at low pH was removed and the short chain phospholipids remaining in the outer monolayer were back extracted with DOPC. Two additional control experiments were performed: 1] DLPC (200 μM) was incorporated into cells as described above for 15 min and then back extracted with DOPC vesicles, and 2] cells without exogenously added lipid were incubated with DOPC vesicles under the conditions of the back extraction assay. In each of the forgoing experiments aliquots were removed at the prescribed time points and the morphological index was determined by light microscopy.

RESULTS

Synthesis and Characterization of pH-Labile Aminophospholipid Derivatives

Maleyl-PE and -PS derivatives were synthesized from the corresponding anhydride in the presence of an appropriate base. The reactions of maleic and phthalic anhydride with DOPE went to completion within 3 h. The desired products were purified to homogeneity using carboxymethyl cellulose cation exchange chromatography. The reactions of citraconic anhydride with DOPE and with DOPS were complete within 48 h and consistently resulted in initial yields between 72% and 79%. 1H-NMR chemical shifts and mass spectrometry data for the maleyl-DOPE (M-DOPE), phthalyl-DOPE (P-DOPE), C-DOPE, C-DOPS, and C-DLPS derivatives (Table I) are consistent with the predicted structures. For the citraconyl derivatives, only a single olefinic proton resonance was observed, consistent with a single positional isomer, most likely with the olefinic methyl adjacent to the carboxyl group.

The syntheses of (D-DOPE) and (T-DOPE) resulted in lower yields (Table I) compared with other maleyl-lipid derivatives. This was consistent with previous reports that dimethylmaleyl-amino acids were particularly unstable (Dixon & Perham, 1968). However, both mass spectrometry and NMR data were not consistent with data anticipated for D-DOPE and T-DOPE. Mass spectrometry data indicated a parent ion peak for these derivatives which was 16 amu lower than the molecular weights of the expected products. NMR data indicated the presence of a single proton resonance in D-DOPE and two such resonances in T-DOPE for the caging group, suggesting a symmetric configuration of the blocking group. These results are consistent with the cyclization of the maleyl blocking groups to the corresponding imides.

Synthesis of $^3$H Labeled DOPS and C-DOPS

DOP$^3$HS was synthesized from DOPC and L-[3-$^3$H]-serine by phospholipase D catalyzed transphosphatidylation (Juneja et al., 1989) at a final yield of 34%. DOP$^3$HS was acylated with citraconic anhydride to form citraconyl-DOP$^3$HS for a yield of 82.4% after 48 h at 25° C. CM-52 chromatography of the mixture yielded 11.4 $\mu$Ci of the purified product.

pH-Dependent Cleavage of "Caged" Aminophospholipids

Figure 1:
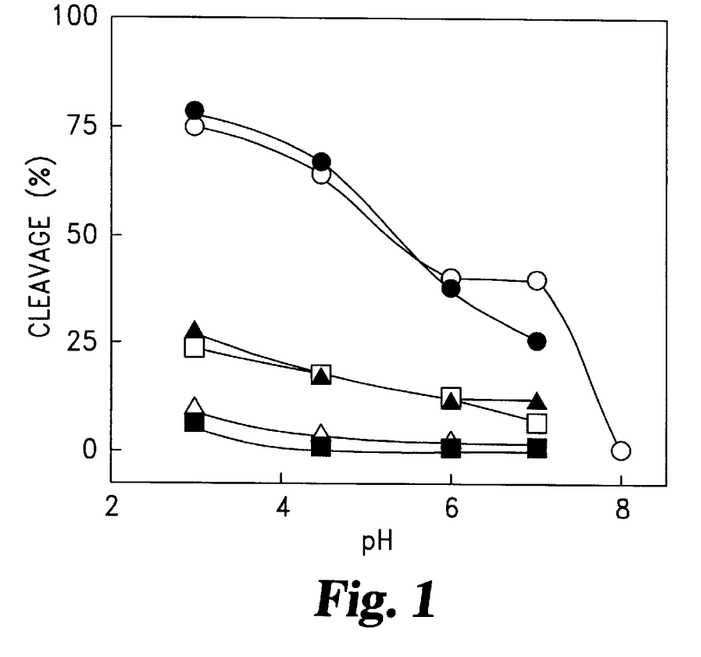
FIG. 1 shows the pH-Dependent cleavage of maleyl-aminophospholipids. Derivatized aminophospholipids (C-DOPS (open circles), C-DOPE (filled circles), M-DOPE (open squares), D-DOPE (filled squares), T-DOPE (open triangles), and P-DOPE (filled triangles), 0.5 mM each) were suspended in citrate (pH 3, 4.5 and 6 ) or Hepes (pH 7 and 8) buffer and incubated for 1 h at 37° C. The extent of hydrolysis was determined by phosphate analysis of thin layer chromatographic separations of extracted lipids.

The pH dependence of cleavage of the DOPS and DOPE derivatives was determined by incubating lipid dispersions (MLVs) in buffers of varying pH for 1 h at 37° C. Hydrolysis was measured by phosphate analysis of TLC-separated products. The T-DOPE and D-DOPE derivatives were not cleaved to any appreciable extent at any pH (FIG. 1). Significant cleavage of the phthalic and maleic DOPE derivatives did not occur at the most physiologically desirable pH values (pH 5.5–8); however, 25% cleavage was observed after extended incubation at pH 3. Half-maximal cleavage for the C-DOPE and C-DOPS derivatives was observed at pH 5.5 and pH 6.5, respectively. The stability of these derivatives demonstrated a much steeper dependence on pH than that observed for the other maleyl derivatives. Because the citraconyl derivatives were cleaved significantly in a physiologically relevant pH range, they were chosen for further characterization.

The time course for hydrolysis of "caged" aminophospholipids measured in citrate buffer (pH 5.5) at 37° C.

Figure 2:
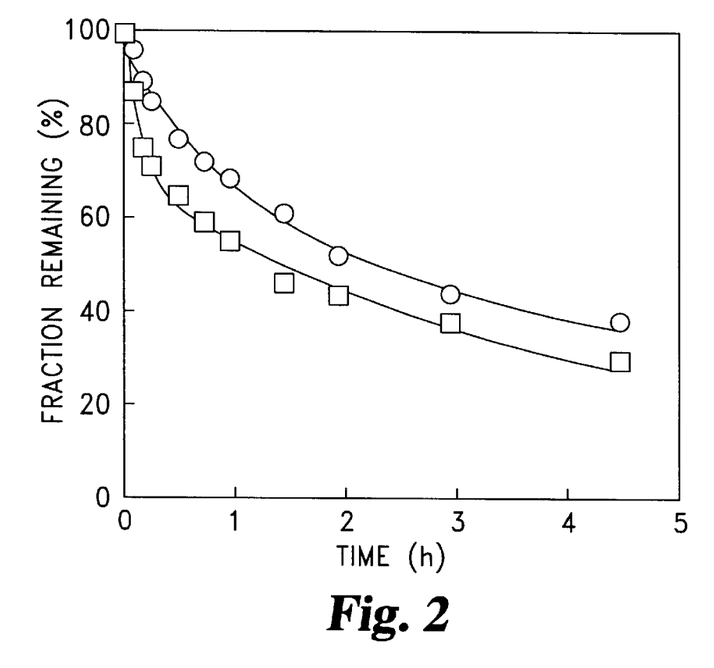
FIG. 2 shows timecourse of cleavage of citraconyl-aminophospholipids. C-DOPE (open circles) and C-DOPS (open squares) were suspended in citrate buffer (pH 5.5) and incubated at 37° C. for the indicated time. The extent of cleavage was determined by phosphate analysis of thin layer chromatographic separations of extracted lipids. The solid lines are non-linear least square fits of the data to a double exponential equation $$(f(x)=\alpha 1*\exp(-x/\tau 1)+\alpha 2*\exp(-x/\tau 2)).$$

The half-time for cleavage of C-DOPE and C-DOPS was 110 min and 85 min, respectively (FIG. 2). The data do not describe well a single exponential decay, as expected of an intramolecular reaction. However, the data fit well to a biexponential equation $$f(x)=\alpha 1^*\exp(-x/\tau 1)+\alpha 2^*\exp(-x/\tau 2)).$$

The cleavage of C-DOPE consists of a initial fast component ($\tau 1$=0.9 h) and a slower component ($\tau 2$=7 h). The cleavage of C-DOPS was 6-fold faster than C-DOPE initially ($\tau 1$=0.15 h), yet consisted of a slow component of similar rate to C-DOPE ($\tau 2$=4.8 h).

Although the present invention is not limited by any theory, several hypotheses were tested to explain the biexponential nature of cleavage. The different rates could have been a result of differential extraction of the modified and unmodified lipids after exposure to low pH. However, in control experiments, the extraction procedure employed (Comfurius & Zwaal, 1977) resulted in the recovery of greater than 90% of DOPE, DOPS, and the citraconyl derivatives. Alternatively, the different rates could have been due to the presence of additional isomers of the citraconyl group, such as the trans isomer or the positional isomer in which the methyl group is adjacent to the carboxyl, rather than the amide, group. However, TLC and NMR data did not suggest the presence of any additional components: only one component was apparent by TLC in three different solvent systems (CHCl3:CH3OH:H2O (25:10:1), CHCl3:CH3OH:H2O:NH4OH (65:25:2.5:2.5), and CH3OH:CH3CN (7:3)) and the NMR spectra indicated only a single resonance for the olefinic proton of the citraconyl blocking group.

Figure 3:
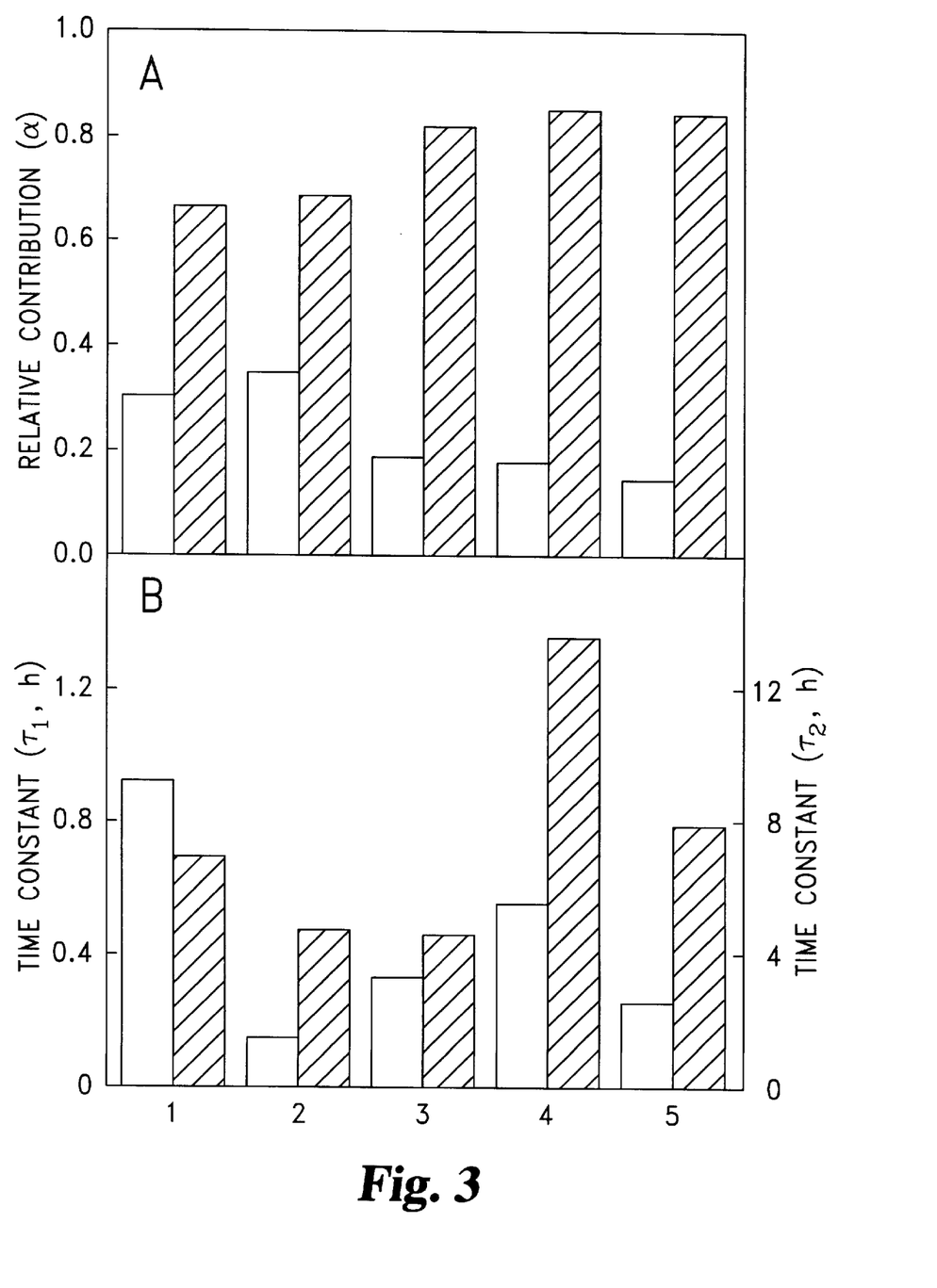

A blocking hypothesis is the presence of multiple lipid environments, such as a mixture of multilamellar vesicles (MLVs) and small unilamellar vesicles (SUVs). The surface potential, and thus the pH at the membrane interface, may be different at the outer bilayer compared to the inner bilayers of MLVs, resulting in multiple rates of cleavage. This hypothesis was tested by solubilizing the lipid with Triton X-100 (0.1%) so that all the lipid was present in the form of phospholipid-detergent mixed micelles. Under these conditions, biphasic hydrolysis was also observed, although accompanied by a 2-fold increase in $\tau 1$ (FIG. 3), indicating that the heterogeneous lipid organization was not responsible for the biphasic cleavage kinetics.

The effect of surface potential on cleavage was investigated by increasing the ionic strength (1 M NaCl) or by diluting the surface charge density with a 5-fold excess of egg PC. Both of these conditions result in an increase in pH at the membrane interface (Tocanne & Teissié, 1990). Again, biphasic cleavage kinetics were observed, however both the slow and the fast rates were equally sensitive to changes in the pH at the membrane interface: a 2.8 to 3.5-fold increase in both $\tau 1$ and $\tau 2$ occurred in the presence of 1 M NaCl, while a smaller increase (1.6-fold) was observed in samples diluted with egg PC.

Another explanation is that the reverse reaction is appreciable, perhaps due to accumulation of citraconic anhydride (see Scheme 1). This hypothesis was tested by using nucleophilic scavengers to trap the released anhydride. Both water soluble (dithiothreitol, ethanol) and lipophilic (aniline, p-nitroaniline, and DOPE) scavengers were added to C-DOPS solutions and cleavage was measured at a timepoint when the slow rate of cleavage predominated (Table II). None of these scavengers attenuated the slower second rate, indicating that this mechanism likely does not explain the biphasic kinetics. Furthermore, in the presence of DOPE, no formation of C-DOPE was observed by TLC analysis, further indicating the absence of citraconic anhydride released by C-DOPS.

A final hypothesis is the presence of a competing pH dependent reaction, such as isomerization of the cis blocking group to the more stable trans derivative. The two rates must be on the same order of magnitude in order to complete effectively in the first 15–20 min of the cleavage reaction. Thus, the fast rate may include both cleavage of the cis compound and isomerization to the trans isomer. The slow rate may be either the reverse trans to cis isomerization, the slow hydrolysis of the trans isomer by water, or a combination of both.

To test this hypothesis, lipids were isolated from C-DOPE and C-DOPS cleavage reactions at long times, when the slow rate predominates (>30 min), and isolated by CM-52 cation exchange chromatography. Mass spectrometry of the purified component confirms the presence of a molecule with the same molecular weight as the starting material (data not shown), eliminating the possibility that the competing pH-dependent reaction was cyclization to the imide. Instead, NMR data shows an upfield shift of the olefinic proton resonance in the blocking group (from 5.702 to 5.445 ppm for C-DOPE and from 5.663 ppm to 5.643 ppm for C-DOPS), consistent with a cis to trans conversion.

Incorporation and Uncaging of Citraconyl-DOPS in Human Erythrocytes

Figure 4A:
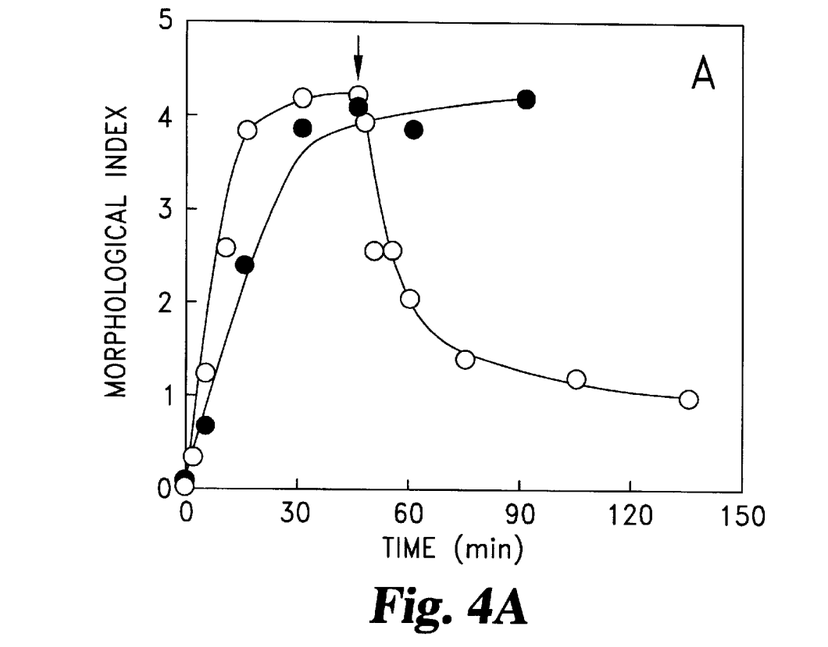
Figure 4B:
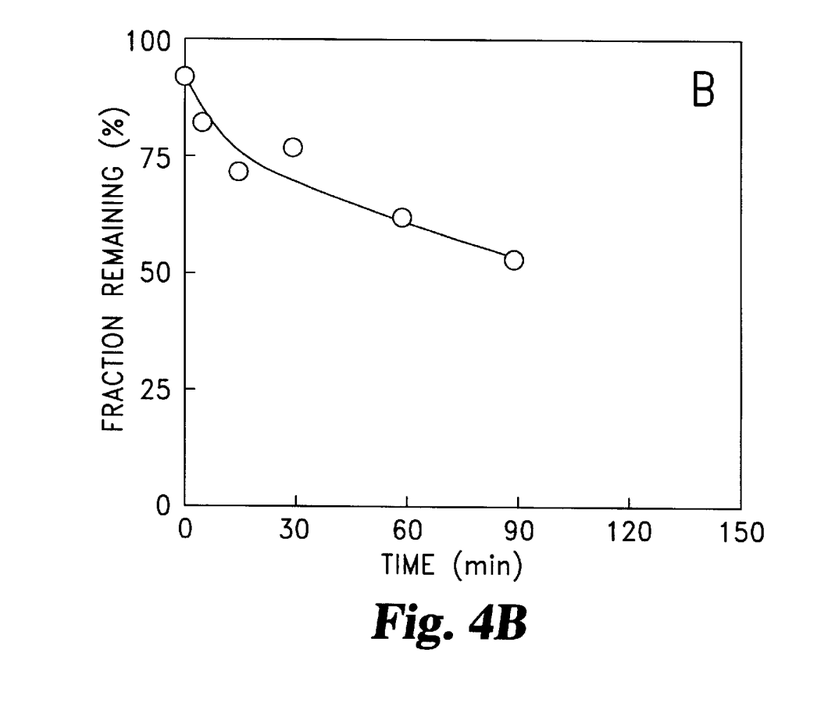

Uncaging of the C-DOPS derivative was measured in human red blood cells in order to test the feasibility of using the compound as a probe of aminophospholipid transport in biological membranes. Incorporation and transbilayer movement of C-DOPS were examined by monitoring changes in cell morphology. Cells treated with C-DOPS in HBS remain echinocytic for more than 1.5 h (FIG. 4A). When the Hepes buffer was exchanged for a citrate buffer (pH 5.5) the cells reverted to a more discoid shape, consistent with hydrolysis of a fraction of the C-DOPS to DOPS, followed by transport to the inner monolayer. Cleavage of C-DOP$^3$HS was measured directly in intact erythrocytes. Cells were treated with C-DOP$^3$HS (61 nCi) for 1 h at 37° C. in HBS. Following exchange with citrate buffer (pH 5.5), the cells were incubated at 37° C. and hydrolysis was measured by analysis of extracted lipids separated by thin layer chromatography. Cleavage of C-DOP$^3$HS (FIG. 4B) followed a similar timecourse and extent in erythrocytes as in model membranes (see FIG. 2) and is consistent with the morphological changes induced in C-DOPS treated cells (FIG. 4A).

Dependence of PS Transport on pH

Figure 5:
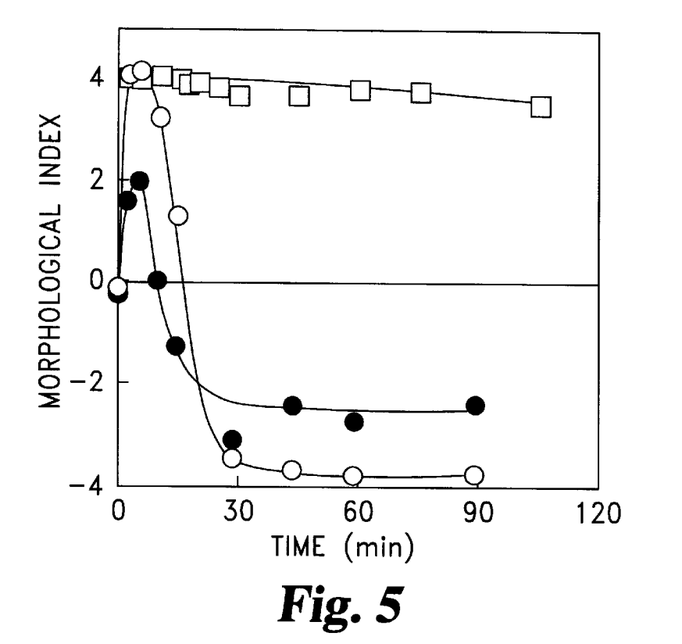
FIG. 5 shows the effect of pH on DLPS transport. Washed human erythrocytes were incubated with sonicated suspensions of DLPS (200 μM, open circles, filled circles) or DLPC (200 μM, open squares) in citrate buffer pH 5.5 (open symbols) or in HBS (filled symbols) at 37° C. Aliquots were fixed with glutaraldehyde and analyzed by light microscopy.

To determine if erythrocyte shape changes and PS transport were influenced by external pH, cells were treated with DLPC and DLPS in citrate buffer (pH 5.5) or HBS. Cells treated with DLPC (200 μM) in citrate buffer became echinocytic within 2 min and retained their echinocytic shape for more than 1.5 h (FIG. 5), similar to shape changes induced in DLPC treated cells at higher pH (data not shown). Cells treated with DLPS (200 μM) in HBS or citrate buffer became echinocytic initially but rapidly reverted to stomatocytes, indicating transport of DLPS from the outer to the inner monolayer at both pH values.

Back-Extraction of Incorporated Lipid

Figure 6:
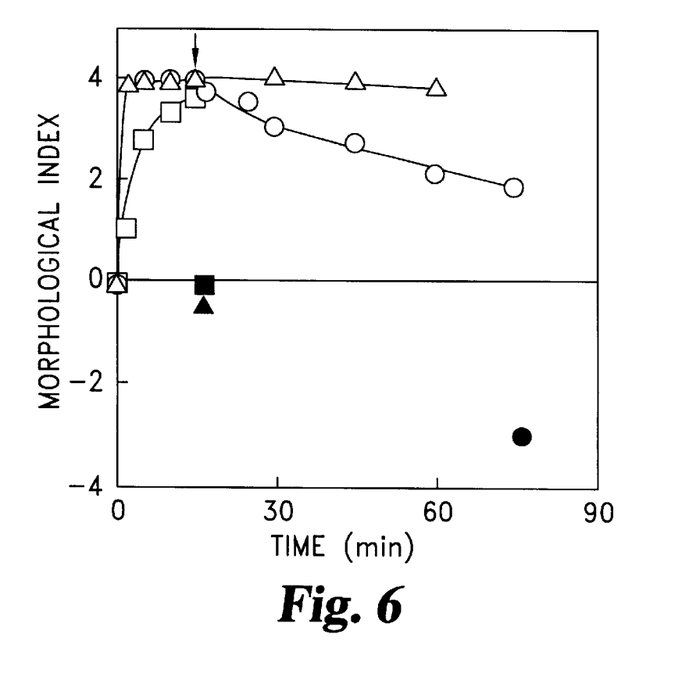
FIG. 6 shows the incorporation, uncaging and transport of C-DLPS in human erythrocytes. Timecourse of erythrocyte shape change (MI) induced by suspensions of C-DLPS (200 μM, open circles, open triangles) and DLPC (200 μM, open squares) in HBS. After 15 min (arrow), one sample of cells (open circles) was centrifuged, resuspended in citrate buffer (100 mM, pH 5.5) and re-incubated at 37° C. At 15 or 75 min, aliquots of each sample were removed and treated with DOPC vesicle (20 mM, 5% HCT) for 15 min at 37° C (closed symbols). At the indicated times aliquots were fixed with glutaraldehyde and analyzed by light microscopy.

The transbilayer distribution of DLPS, DLPC, and C-DLPC before and after low pH treatment was verified by back extraction of residual outer monolayer dilauroyl phospholipids with exogenous DOPC vesicles (Daleke & Huestis, 1989). When lipid was back extracted after incorporation of C-DLPS into the outer monolayer in HBS, the cells reverted to discocytes, indicating that all of the lipid was in the inner monolayer (FIG. 6). DLPC, which is not transported rapidly across the erythrocyte membrane, gave identical results. When cells treated with C-DLPS for 15 min were subjected to low pH for an additional 60 min, the cells reverted to stomatocytes upon back-extraction with DOPC vesicles. These results indicate that C-DLPS remains in the outer monolayer in HBS, but that a portion of the lipid transverses the membrane in citrate buffer and accumulates in the inner monolayer, consistent with low pH-induced "uncaging" and flippase-mediated transport of C-DLPS.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

TABLE I

Physical characteristics of synthetic "caged" aminophospholipids[a]

| compound | yield (%) | m.w. (calc) | m.w. (m/e) | parent ion | NMR chemical shifts (blocking group only) |
|---|---|---|---|---|---|
| maleyl-DOPE | 100 | 840 | 840 | M-H | δ 6.43 (s, H$_a$) |
|  |  |  | 862 | M-Na + 2H | δ 5.67 (s, H$_b$) |
| dimethyl-maleyl-DOPE | 67 | 866 | 850 | M-O-H | δ 1.93 (s, CH$_3$) |
| tetrahydro-phthlalyl-DOPE | 47 | 892 | 876 | M-O-H | δ 1.66 (m, CH$_2$) |
|  |  |  | 899 | M + Na-O-H | δ 2.21 (m, CH$_2$) |
| phthalyl-DOPE | 100 | 890 | 890 | M-H | δ 7.317 (m), |
|  |  |  |  |  | δ 7.401 (m) |
|  |  |  | 912 | M + Na-2H | δ 7.599 (m), |
|  |  |  |  |  | δ 7.317 (m) |
| citraconyl-DOPE | 77 | 854 | 854 | M-H | δ 1.887 (s, CH$_3$) |
|  |  |  | 876 | M-Na + 2H | δ 5.702 (s, H) |
| citraconyl-DOPS | 78 | 899 | 898.6 | M-H | δ 1.867 (s, CH$_3$) |
|  |  |  | 920.6 | M + Na-2H | δ 5.663 (s, H) |
|  |  |  | 942.6 | M + 2Na-3H |  |
| citraconyl-DLPS | 84 | 735 | 734.9 | M-H |  |
|  |  |  | 756 | M-Na-2H |  |

[a]Aminophospholipid derivatives were synthesized from DOPE, DOPS or DLPS and the appropriate anhydride in the presence of 2,6-lutidine. Mass spectral analysis was performed by negative ion fast atom bombardment.

TABLE II

Effect of nucleophilic scavengers on the pH-dependent hydrolysis of C-DOPS[a]

|  |  | time | % cleavage | |
|---|---|---|---|---|
| scavenger | concentration | (h) | +scavenger | −scavenger |
| dithiothreitol | 5 mM | 3 | 56.6 | 63.5 |
| ethanol (v/v) | 0.05% | 3 | 57.9 | 63.5 |
|  | 0.1% | 3 | 56.9 | 63.5 |
|  | 0.5% | 3 | 57.3 | 63.5 |
|  | 1.5 mM | 2.5 | 56.5 | 55.2 |
| p-nitroaniline | 1.5 mM | 2.5 | 55.7 | 55.2 |
| DOPE | 2.5 mM | 3 | 34.3 | 58.0 |

[a]Multilamellar vesicle suspensions of C-DOPS were treated with citrate buffer (pH 5.5) in the presence or absence of the indicated concentration of scavenger for the indicated times. The fraction of cleaved C-DOPS was determined by phosphate analysis of TLC-separated lipids.

REFERENCES

The following references are indicative of the level of ordinary skill in the art and are hereby incorporated by reference in their entirety as if each has been incorporated by reference and fully set forth.

Barlett, G. (1959) J. Biol. Chem. 234, 466–468.
Bitbol, M., Fellmann, P., Zachowski, A. & Devaux. P. F. (1987) Biochim. Biophys. Acta 904, 268–282.
Bretscher, M. S. (1973) Science 181, 622–629.

Colleau, M., Hervé, P. Fellmann, P. & Devaux, P. F. (1991) Chem. Phys. Lip. 57, 29–37.
Comfurius, P. & Zwaal, R. F. A. (1977) Biochim. Biophys. Acta 488, 36–42.
Connor, J. & Schroit, A. J. (1987) Biochemistry 26, 5099–5105.
Daleke, D. L. & Huestis, W. H. (1985) Biochemistry 24, 2406–2416.
Daleke, D. L. & Huestis, W. H. (1989) J. Cell Biol. 108, 1375–1385.
Devaux, P. F. (1991) Biochemistry 30, 1163–1173.
Dixon, H. B. F. & Perham, R. N. (1968) Biochem. J. 109, 312–314.
Franck, P. F. H., Bevers, E. M., Lubin, B. H., Comfurius, P., Chiu, D. T. -Y., Op den Kamp, J. A. F., Zwaal, R. F. A., van Deenen, L. L. M. & Roelofsen, B. (1985) J. Clin. Invest. 75, 183–190.
Gerads, I., Govers-Riemslag, J. W. P., Tans, G., Zwaal, R. F. A. & Rosing, J. (1990) Biochemistry 29, 7967–7974.
Gilbert, G. E., Drinkwater, D., Barter, S. & Clouse, S. B. (1992) J. Biol. Chem. 267, 15861–15868.
Haest, C. W. M., Plasa, G., Kamp, D. & Deuticke, B. (1978) Biochim. Biophys. Acta 509, 21–32.
Harris, W. E. (1985) Biochemistry 24, 2873–2883. Homan, R. & Pownall, H. J. (1988) Biochim. Biophys. Acta 938, 155–166.
Juneja, L. R., Kazuoka, T., Goto, N., Yamane, T. & Shimizu, S. (1989) Biochim. Biophys. Acta 1003, 277–283.
Kornberg, R. D. & McConnell, H. M. (1971) Biochemistry 10, 1111–1120.
Krishnaswamy, S. (1990) J. Biol. Chem. 265, 3708–3718.
Martin, O. & Pagano, R. E. (1987) J. Biol. Chem. 262, 5890–5898.
Middlekoop E., Lubin, B. H., Op den Kamp, J. A. F. & Roelofsen, B. (1986) Biochim. Biophys. Acta 855, 421–424.
Morrot, G., Hervé, P., Zachowski, A., Fellman, P. & Devaux, P. (1989) Biochemistry 28, 3456–3462.
Newton, A. C. & Koshland, D. E. (1989) J. Biol. Chem. 264, 14909–14915.
Newton, A. C. & Koshland, D. E. (1990) Biochemistry 29, 6656–6661.
Niggli, V., Adunyah, E. S. & Carafoli, E. (1981) J. Biol. Chem. 256, 8588–8592.
Niggli, V., Adunyah, E. S., Penniston, J. T. & Carafoli, E. (1981) J. Biol. Chem. 256, 395–401.
Rothman, J. E. & Lenard, J. (1977) Science 195, 743–753.
Schroit, A. J. & Zwaal, R. F. A. (1991) Biochim. Biophys. Acta 1071, 313–329.
Seigneuret, M. & Devaux, P. F. (1984) Proc. Natl. Acad. Sci. USA 81, 3751–3755.
Sheetz, M. P. & Singer, S. J. (1974) Proc. Natl. Acad. Sci. USA 71, 4457–4461.
Tilley, L., Cribier, S., Roelofsen, B., Op den Kamp, J. A. F. & van Deenen, L. L. M. (1986) FEBS Lett. 194, 21–27.
Tocanne, J. -F. & Teissié, J. (1990) Biochim. Biophys. Acta 1031, 111–142.
Wheeler, K. P. & Whittam, R. (1970) J. Physiol. 207, 303–328.
Van Meer, G. & Op den Kamp, J. A. F. (1982) J. Cell. Biochem. 19, 193–204.
Verkleij, A. J., Zwaal, R. F. A., Roelofsen, B., Comfurius, P., Kastelijn, D. & van Deenen, L. L. M. (1973) Biochim. Biophys. Acta 323, 187–193.
Zachowski, A., Favre, E., Cribier, S., Hervé, E. & Devaux, P. F. (1986) Biochemistry 25, 2285–2590.

What is claimed is:

1. A pH-sensitive liposomal delivery system, comprising a liposome containing an active agent, said liposome being formed with one or more aminophospholipids having the formula I or II:

wherein $Z$=—$CH_2$— or —$C(H)(COO^-)$—;

$Y$=—H or lower alkyl; and $R^1$ and $R^2$, which may be the same or may differ from one another, each provides the aminophospholipid with a fatty acid group.

2. The delivery system of claim 1 wherein said one or more aminophospholipid is of the formula II.

3. The delivery system of claim 1 wherein said one or more aminophospholipid is of the formula I.

4. The delivery system of claim 3 wherein Z is —$CH_2$—.

5. The delivery system of claim 3 wherein Z is —$C(H)(COO^-)$—.

6. The delivery system of claim 3 wherein Y is lower alkyl.

7. The delivery system of claim 6 wherein Y is methyl.

8. The delivery system of claim 6 wherein $R^1$ and $R^2$ are each a saturated fatty acid group having about 12 to about 24 carbon atoms.

9. The delivery system of claim 8 wherein Z is —$CH_2$—.

10. The delivery system of claim 8 wherein Z is —$C(H)(COO^-)$—.

11. The delivery system of claim 9 wherein Y is methyl.

12. The delivery system of claim 10 wherein Y is methyl.

13. A method of introducing a modified aminophospholipid into a cell, comprising contacting the cell with an aminophospholipid compound of the formula I or II -continued

II wherein

Z=—CH₂— or —C(H)(COO⁻)—;

Y is —H or lower alkyl; and

R¹ and R², which may be the same or may differ from one another, each provides the aminophospholipid with a fatty acid group, at a pH sufficient to induce cell infusion.

14. The delivery system of claim 1 wherein the group incorporates a spin label, a radioactive label or a fluorescent label.

15. The method of claim 13 wherein the group incorporates a spin label, a radioactive label or a fluorescent label.

* * * * *

UNITED STATES PATENT AND TRADEMARK OFFICE
Certificate

Patent No. 5,972,380                                    Patented: October 26, 1999

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: David L. Daleke, Bloomington, IN (US); Daryl C. Drummond, Pacifica, CA (US); and Robert M. Straubinger, Amherst, NY (US).

Signed and Sealed this Fifth Day of February 2008.

JULIE BURKE
*Special Program Examiner*
Technology Center 1600